United States Patent [19]

Kajiwara et al.

[11] Patent Number: 5,916,537
[45] Date of Patent: Jun. 29, 1999

[54] DIAGNOSTIC AND DIAGNOSIS METHOD FOR CENTRAL NERVOUS ABNORMALITY AND PHENYLKETONURIA

[75] Inventors: Masahiro Kajiwara, Saitama; Tsuyoshi Hirose; Nobuhiro Ikei, both of Tokushima, all of Japan

[73] Assignee: Otsuka Pharmaceutical Co., Ltd., Tokyo, Japan

[21] Appl. No.: 08/809,821

[22] PCT Filed: Aug. 6, 1996

[86] PCT No.: PCT/JP96/02206

§ 371 Date: Apr. 1, 1997

§ 102(e) Date: Apr. 1, 1997

[87] PCT Pub. No.: WO97/05906

PCT Pub. Date: Feb. 20, 1997

[30] Foreign Application Priority Data

Aug. 8, 1995 [JP] Japan .................................. 7-202580
Jan. 19, 1996 [JP] Japan ...................................... 8-7043

[51] Int. Cl.$^6$ .......................... A61K 51/00; A61M 36/14
[52] U.S. Cl. ...................... 424/1.81; 424/1.45; 424/1.11
[58] Field of Search ................... 424/1.11, 1.45, 424/1.65, 1.81

[56] References Cited

U.S. PATENT DOCUMENTS 5,320,825   6/1994   Kung ...................................... 424/1.85
5,386,832   2/1995   Wagner et al. ........................... 128/665
5,707,602   1/1998   Klein ...................................... 424/1.17

FOREIGN PATENT DOCUMENTS 61-42219    9/1986   Japan .
5-142146    6/1993   Japan .
WO 94/28941 12/1994  WIPO .

OTHER PUBLICATIONS

P. Klein, et al., "The Commercial Feasibility of C$^{13}$ Breath Tests," *Analytical Chemistry Symposium Series,* vol. 11, (1982), pp. 347–353.

N. Matsuoka, et al., "Effect of FR 121196, a Novel Cognitive Enhancer, on the Memory Impairment of Rats in Passive Avoidance and Radial Arm Maze Tasks," *J. Pharmacol, Exp. Ther.,* vol. 263, No. 2(1992), pp. 436–445.

G.H. Dodd, "The Lipid Membrane Hypothesis of Schizophrenia: Implications for Possible Clinical Breath Tests," *Prostaglandins, Leukotrienes and Essential Fatty Acids,* vol. 55, Nos. 1 and 2 (1996), pp. 95–99.

H.G. Broesicke, et al., *Chemical Abstracts,* Abstract No. 23791, vol. 119, Jul. 19, 1993.

W.D. Lehmann, et al., "Metabolic Conversion of L–[U–$^{14}$C] phenylalanine to Respiratory $^{14}CO_2$ in Healthy Subjects, Phenylketonuria Heterozygotes and Classic Phenylketonurics," *Clinica Chimica Acta.,* vol. 157, No. 3 (1986), pp. 253–266.

N. Tran–Manh, et al., "Abnormalities in $^{14}CO_2$ Production from DL–3,4–Dihydroxyphenylalanine–arboxyl–$^{14}$C in Schizophrenia and Parkinsonism: A Preliminary Report," *Rev. Can. Biol.,* vol. 31, Supp. (1972), pp. 255–262.

C. Godin, et al., "Tryptophan Metabolism in Normal and Phenylketonuric Rats," *Biochim. Biophys. Acta,* vol. 130 (1966), pp. 535–537.

J.F. Dellaria, Jr., et al., "Stereoselective Alkylation of Chiral Glycine Enolate Synthons. The Enantioselective Synthesis of α–Amino Acid Derivatives," *Tetrahedron Letters,* vol. 29, No. 47 (1988), pp. 6079–6082.

J.L. Howard, et al., "Empirical Behavioral Models of Depression, with Emphasis on Tetrabenazine Antagonism," *Antidepressants: Neurochemical, Behavioral, and Clinical Perspectives,* (Eds. S.J. Enna, Ph.D., et al.) Raven Press, New york, 1981, pp. 107–120.

D.A. Schoeller, et al., "A Microprocessor Controlled Mass Spectrometer for the Fully Automated Purification and Isotopic Analysis of Breath Carbon Dioxide," *Biomedical Mass Spectrometry,* vol. 6, No. 8 (1979), pp. 350–355.

P.D. Klein, et al., "Applications of Stable Isotopes to Pediatric Nutrition and Gastroenterology: Measurement of Nutrient Absorption and Digestion Using $^{13}$C," *Journal of Pediatric Gastroenterology and Nutrition,* vol. 4 (1985), pp. 9–19.

C.J.E. Niemegeers, et al., "Interaction of Drugs with Apomorphine, Tryptamine and Norepinephrine. A New "in vivo" Approach: the ATN–Test in Rats," *Arch. int. Pharmacodyn,* vol. 227 (1977), pp. 238–253.

A.J. Puech, et al., "Pharmacological Properties of New Antipsychotic Agents: use of Animal Models," *Neuropharmacol.,* vol. 20 (1981), pp. 1279–1284.

L. Davis, et al., "Substituted (Pyrroloamino) pyridines: Potential Agents for the Treatment of Alzheimer's Disease," *J. Med. Chem.,* vol. 39, No. 2 (1996), pp. 582–587.

*Primary Examiner*—Jose' G. Dees
*Assistant Examiner*—Dameron Jones
*Attorney, Agent, or Firm*—Finnegan, Henderson, Farabow, Garrett & Dunner, L.L.P.

[57] ABSTRACT

There is provided a diagnostic for central nervous abnormality, comprising a labeled transmitter substance of central nervous system or a labeled precursor of the transmitter substance, whose at least one of carbon atoms is substituted for a carbon isotope wherein the diagnostic is useful for diagnosing a central nervous abnormality (e.g. depression, Alzheimer's disease, schizophrenia, etc.) by applying it to a living body by oral administration or injection and examining a change in an amount of the carbon isotope in a breath of the living body.

15 Claims, 3 Drawing Sheets

DIAGNOSTIC AND DIAGNOSIS METHOD FOR CENTRAL NERVOUS ABNORMALITY AND PHENYLKETONURIA

This application is a 371 of PCT/JP96/02206 filed Aug. 6, 1996.

TECHNICAL FIELD

The present invention relates to a diagnostic comprising a labeled transmitter substance of a central nervous system or a labeled precursor of the transmitter substance, whose a specific carbon atom is replaced by a carbon isotope, which is used for diagnosing a central nervous abnormality and phenylketonuria by measuring an amount of the carbon isotope in a breath of the living body to which the diagnosis has been administered, and a diagnosis method using the above diagnostic.

BACKGROUND ART

Heretofore, various morbidities with respect to a central nerve, such as depression, Alzheimer's disease, schizophrenia, etc. have been generally referred to as a "central nervous abnormality". Various pharmacological and biological studies on this central nervous abnormality have been made, and the study on a novel drug for treating these diseases by normalizing a metabolic change has also been made.

Phenylketonuria is a morbidity caused by dysbolism of phenylalanine.

However, the elucidation of the mechanism of pathopoiesis and metabolic change have never been sufficiently conducted, and a method for simply and precisely diagnosing these diseases has never been established.

DISCLOSURE OF THE INVENTION

It is an object of the present invention to provide a method for simply and precisely diagnosing diseases which are generally referred to as a central nervous abnormality and phenylketonuria, and a diagnosis used for diagnosing these diseases.

The present inventors have intensively studied so as to accomplish the above object. As a result, it has been found that, when a drug containing, as an active ingredient, a labeled transmitter substance of a central nervous system or a labeled precursor of the transmitter substance, whose at least one carbon atom is substituted for a carbon isotope, is administered to a living body and then an amount of carbon isotope in a breath is measured, the amount of carbon isotope reflects the central nervous abnormality and, therefore, the above drug is useful as a diagnostic for central nervous abnormality. Accordingly, when using this diagnostic, the central nervous abnormality can be simply, quickly and very precisely diagnosed by a simple operation without accompanying invasion of a subject.

That is, according to the present invention, there is provided a diagnostic for diagnosing central nervous abnormality, comprising the labeled transmitter substance of the central nervous system or a labeled precursor of the transmitter substance, whose at least one carbon atom is substituted for the carbon isotope, wherein the diagnostic is used for diagnosing central nervous abnormality by applying the diagnostic to a living body due to oral administration or injection, and examining a change in the amount of the carbon isotope in a breath of the living body. Further, there is also provided a diagnosis method using the diagnostic mentioned above.

Phenylalanine, which is included in the transmitter substance of central nervous system or its precursor, is related to phenylketonuria. Therefore, when a drug containing phenylalanine labeled with a carbon isotope at at least one of the 1-position, 2-position and 3-position of the side chain as an active ingredient is administered to a living body and then an amount of carbon isotope in a breath of the living body is measured, the amount of carbon isotope reflects the phenylketonuria. Therefore, the above drug is also useful as a diagnostic for phenylketonuria. Accordingly, when using this diagnostic, the phenylketonuria can be easily, quickly and very precisely diagnosed by a simple operation without accompanying invasion of a subject.

That is, according to the present invention, there are provided a diagnostic for phenylketonuria, comprising phenylalanine labeled with a carbon isotope at at least one of the 1-position, 2-position and 3-position of the side chain as an active ingredient, wherein the diagnostic is used for diagnosing a phenylketonuria by applying the diagnostic to the living body by oral administration or injection, and examining a change in an amount of the carbon isotope in a breath in a living body, and a diagnosis method using the same.

The diagnosis method using the diagnostic of the present invention is a method using the breath of the subject as a specimen. Therefore, the method has an advantage that the specimen itself can be easily collected without injuring the body in comparison with a conventional diagnosis method using blood as the specimen, and that operations for diagnosis, such as preliminary pretreatment of the specimen are not required.

BEST MODE FOR CARRYING OUT THE INVENTION

Figure 1:
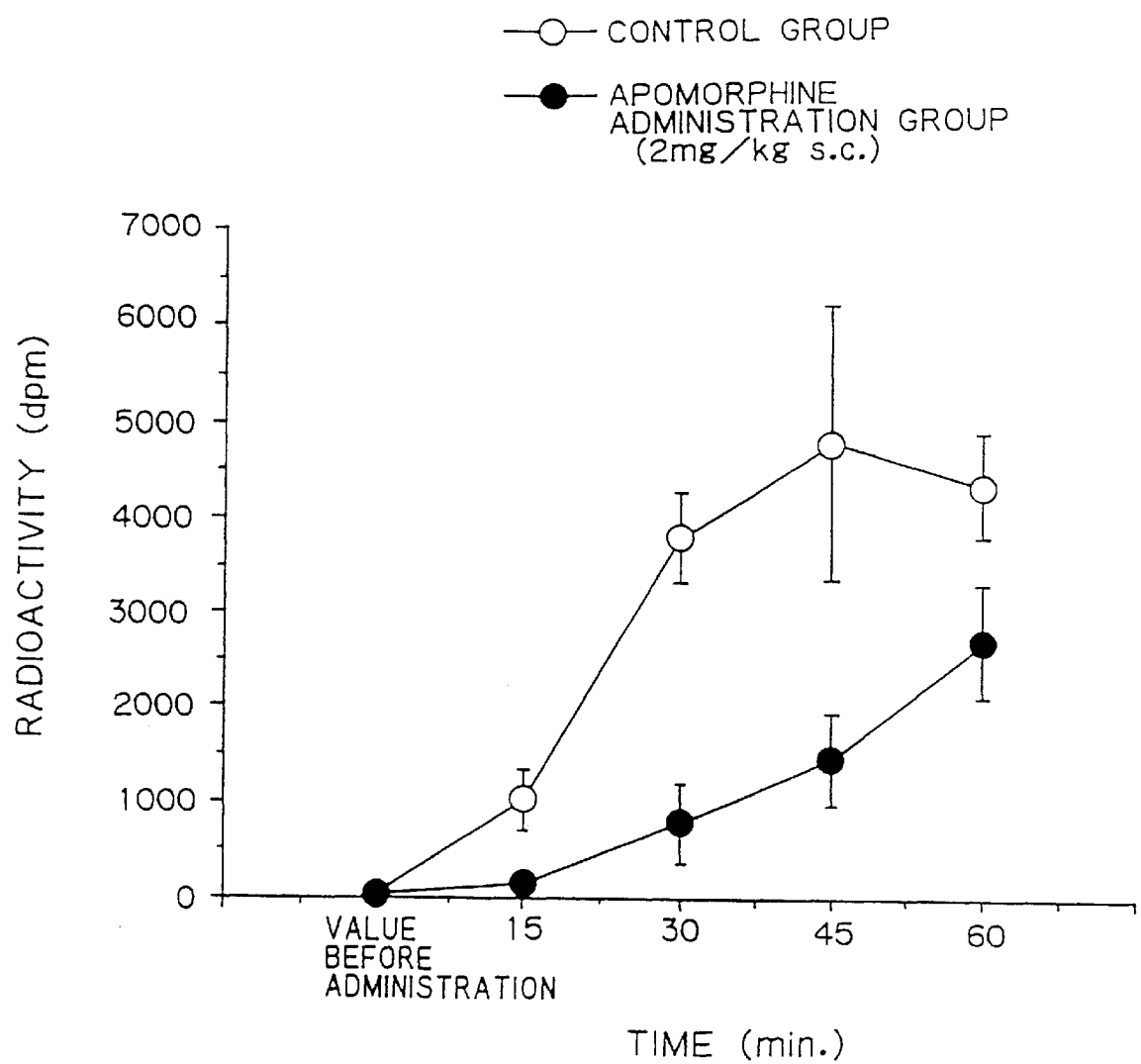
FIG. 1 is a graph illustrating a change in radioactivity of $^{14}CO_2$ in a breath with time after administering $^{14}C$-phenylalanine in the animal model of schizophrenia.

The diagnostic for diagnosing central nervous abnormality of the present invention contains a substance prepared by labeling a transmitter substance of central nervous system or its precursor with a carbon isotope, as an active ingredient. The carbon isotope may be a non-radioactive carbon isotope such as $^{13}C$ or a radioactive carbon isotope such as $^{11}C$ and $^{14}C$. The labeling of the transmitter substance or its precursor with these isotopes can be conducted according to a normal process, for example, process by Dellaria et al. [Dellaria, J. F., Santarsiero, B. D., Tetrahedron Lett., 29, 6078 (1988)]. Some transmitter substances of central nervous system prepared by labeling with these carbon isotope are commercially available. For example, phenylalanine labeled with $^{13}C$ at the I-position, 2-position or 3-position of the side chain is commercially available from CIL Company.

The transmitter substance of central nervous system or its precursor, which is labeled with the above carbon isotope, is selected from the substance related to central nervous abnormality. Typical examples thereof include catecholamine substance such as phenylalanine, tyrosine, dopa, dopamine, norepinephrine (noradrenalin) and epinephrine (adrenalin);

serotonin substance such as tryptophan and 5-hydroxyindoleacetic acid; histamine substance such as histidine; choline substance such as choline, phosphatidylcholine and acetylcholine; and amino acid such as glutamic acid, aspartic acid, γ-amino butyric acid, glycine and taurine.

In labeling the catecholamine substance and serotonin substance, at least one of carbon atoms of the side chain substituted on the aromatic ring or heterocycle may be replaced by the carbon isotope. In labeling the choline substance, a N-methyl group or a carbon atom at 1-position or 2-position of choline skeleton may be replaced by the carbon isotope.

The diagnostic of the present invention can be prepared according to a conventional process except for containing the above labeled transmitter substance of central nervous system or a labeled precursor of the transmitter substance as the active ingredient. For example, the diagnostic can be formed into a dosage form suitable for ingestion of the subject by using the labeled transmitter substance of central nervous system or a labeled precursor of the transmitter substance in combination with a suitable liquid diluent or a solid carrier. The dosage unit form may be the same form as that of a conventional drug or food and drink.

More specific examples of the form of the drug include dosage unit form prepared by using normal diluents or excipients such as fillers, extenders, binders, moistening agents, disintegrators, surfactants, lubricants, etc. Typical examples thereof include tablets, pills, powders, solutions, suspensions, emulsions, granules, capsules, suppositories and injections (e.g. solutions, suspensions, etc.).

When shaping into the form of tablets, as the carrier for preparation, there can be used excipients such as lactose, sucrose, sodium chloride, glucose, urea, starch, calcium carbonate, kaolin, crystalline cellulose, silicic acid, potassium phosphate, etc.; binders such as water, ethanol, propanol, simple syrup, glucose solution, starch solution, gelatin solution, carboxymethyl cellulose, hydroxypropyl cellulose, methyl cellulose, polyvinyl pyrrolidone, etc.; disintegrators such as carboxymethyl cellulose sodium, carboxymethyl cellulose calcium, low-substitution degree hydroxypropyl cellulose, dried starch, sodium alginate, agar powder, laminaran powder, sodium bicarbonate, calcium carbonate, etc.; surfactants such as polyoxyethylene sorbitan fatty acid ester, sodium lauryl sulfate, monoglyceride stearate, etc.; disintegration inhibitors such as sucrose, stearin, cacao butter, hydrogenated oil, etc.; absorption accelerators such as quaternary ammonium base, sodium lauryl sulfate, etc.; humectants such as glycerin, starch, etc.; absorbents such as starch, lactose, kaolin, bentonite, colloidal silicic acid, etc.; and lubricants such as purified talc, stearate, borax, polyethylene glycol, etc. Furthermore, tablets can be optionally formed into tablets subjected to normal tablet coating, such as sugar coated tablets, gelatin coated tablets, enteric coated tablets, film coated tablets, or double tablets and multilayer tablets.

When shaping into the form of pills, as the carrier for preparation, there can be used excipients such as glucose, lactose, starch, cacao butter, hardened vegetable oil, kaolin, talc, etc.; binders such as gum arabic, tragacanth powder, gelatin, ethanol, etc.; and disintegrators such as laminarane, agar, etc. When shaping into the form of suppositories, as the carrier for preparation, there can be used polyethylene glycol, cacao butter, higher alcohol, esters of higher alcohol, gelatin, semisynthetic glyceride, etc. Capsules are normally prepared by mixing a compound as the active ingredient of the present invention with the above various carries for preparation and charging the resulting mixture into a hard capsule, a soft capsule, etc. according to a normal process.

When preparing the drug of the present invention as injections such as solution, emulsion, suspension, etc., it is preferred that the solution, emulsion and suspension are sterilized and are isotonic with blood. When shaping into the form of these solution, emulsion and suspension, as the diluent, there can be used water, ethyl alcohol, macrogol, propylene glycol, ethoxylated isostearyl alcohol, polyoxylated isostearyl alcohol, polyoxyethylene sorbitan fatty acid esters, etc. In this case, sodium chloride, glucose or glycerin may be contained in the drug of the present invention in the amount enough to prepare an isotonic solution, and normal solubilizing agents, buffering agents and soothing agents may be added. If necessary, colorants, preservatives, perfumes, flavors, sweeteners and other drugs may also be contained in the drug of the present invention.

The amount of the above labeled transmitter substance or a labeled precursor of the transmitter substance to be contained in the drug of the present invention is not specifically limited, and can be appropriately selected from a wide range. It is preferred that the substance is normally contained in the pharmaceutical preparation in an amount of about 10 to 300 mg.

The administration method of the drug is not specifically limited, and can be selected according to various forms of preparation, age and sex of the patient, conditions of diseases and other conditions. For example, the tablet, pill, solution, suspension, emulsion, granule and capsule are orally administered. The injection can be intravenously administered as it is or after mixing with a normal fluid replacement such as glucose, amino acid, etc. If necessary, the injection can also be intramuscularly, intracutaneously, subcutaneously or intraperitoneally administered as it is. The suppository is intrarectally administered.

The dose of the preparation is appropriately selected according to direction for use, age and sex of the patient, conditions of diseases and other conditions. The amount of the compound of the present invention as the active ingredient is preferably about 0.5 to 5 mg/kg/day and the preparation can be preferably administered 1 to 4 times per day. The dose of the isotope can be about 100 mg/60 kg of body weight.

The present invention also provide a method for diagnosing a central nervous abnormality (e.g. depression, Alzheimer's disease, schizophrenia, etc.) by using the diagnostic of the present invention thus obtained as described above.

This diagnosis method is carried out by previously administering the diagnostic of the present invention to the subject and measuring the amount of carbon isotope in the breath of the subject.

The amount of carbon isotope, for example, is obtainable by measuring a concentration of carbon dioxide in the breath and examining a concentration of carbon isotope in carbon dioxide, or by measuring radioactivity in the breath.

In the former method, about 250 ml of the breath is directly collected in an aluminum bag at each time where 0, 30, 60, 90, 120, 150 and 180 minutes have passed since the diagnostic of the present invention was administered, and then the breath collected is analyzed and the concentration of carbon dioxide in the breath, particularly concentration of carbon dioxide containing no carbon isotope and that of carbon dioxide containing the carbon isotope are measured.

The measurement of the concentration of carbon dioxide can be conducted according to a conventional method. For example, the measurement of $^{13}CO_2$ can be conducted by a mass spectrometry using a conventional mass spectrometer, more specifically, automatic gas isotope specific mass spectrometer [see "mass spectrometer controlled by microprocessor for completely automated purification and isotope analysis of $CO_2$ in the breath", Biomedical Mass Spectrometry, Vol. 6, 350–355, (1979); G. W. Ewing, Instrumental Methods of Chemical Analysis, (4th edition, 1975)]. The desired measurement of $^{13}CO_2$ can also be conducted by an infrared spectrometry using an infrared spectrophotometer and a nuclear magnetic resonance spectrometery [e.g. (1) see Japanese Patent Publication No. 61-42219, (2) P. Klein et al., "Application of Stable Isotopies to Pediatric Nutrient and Gastroenterology: Measurement of Nutrient Absorption and Digestion Using $^{13}C$" Vol.4 Journal of Pediatric Gastroenterology and Nutrition 9–19 (1985), and (3) P. Klein et al., "The Commercial Feasibility of $^{13}C$ Breath Tests" Vol. 11 Analytical Chemistry Symposium Series 347–353 (1982)]. Furthermore, the measurement of $^{13}CO_2$ can also be conducted by using a spectrometer on the basis of a laser such as semiconductor laser analyzing device [e.g. see Japanese Laid-Open Patent Publication No. 5-142146].

According to the above analyzing methods using various instruments, the concentration of carbon dioxide in the breath can be measured, thereby determining a $^{13}CO_2/^{12}CO_2$ ratio.

The present inventors have found first that there is a significant difference in an amount of $^{13}CO_2$ and $^{13}CO_2/^{12}CO_2$ ratio, which are determined as described above, between a patient suffering from depression, Alzheimer's disease or schizophrenia and a healthy person and, therefore, the above diseases can be diagnosed by using the amount (e.g., represented by concentration or ratio) of the carbon isotope as an index. That is, there have hitherto been reported some examples in the patient suffering from depression, e.g. abnormality such as defect of phenylalaninehydroxylase metabolizing phenylalanine into tyrosine at the liver, reduction in metabolic turnover of tyrosine (reduction in activity of tyrosinetransaminase), etc. However, there has never been reported an example of taking notice of a metabolic function of phenylalanine due to the enzyme defect and diagnosing the abnormality by measuring the concentration of carbon dioxide containing the carbon isotope in the breath. Therefore, the fact that depression can be easily and simply diagnosed with high precision and high sensitivity by such a breath diagnosis method is a novel knowledge which has been found fist by the present inventors.

According to the breath diagnosis method using the diagnostic of the present invention, dementia (e.g. Alzheimer's disease, etc.) and schizophrenia, wherein an effective diagnosis method has never been found heretofore, can also be easily and simply diagnosed with high precision according to the same mechanism as that described above.

Phenylketonuria is broken out by accumulation of phenylalanine in blood or brain without being metabolized. Therefore, according to the method for measuring the breath using the diagnostic comprising phenylalanine labeled with a carbon isotope at at least one of the 1-position, 2-position and 3-position of the side chain as an active ingredient of the present invention, the patient suffering from phenylketonuria can be easily and simply diagnosed with high precision according to the same mechanism as that described above.

INDUSTRIAL APPLICATION

As described above, the present invention provides a novel technique for diagnosing central nervous abnormality and phenylketonuria, and the value of the present invention in the clinical diagnosis is great.

EXAMPLES

The following Test Examples and Examples further illustrate the present invention in detail.

Test Example 1
(Test due to an animal model of schizophrenia)

It was examined whether a metabolism of $^{14}C$-phenylalanine administered orally changes or not by comparing an animal model of schizophrenia with a normal animal, using an amount of $^{14}CO_2$ excreted in a breath as an index.

The animal model of schizophrenia means that in which a stereotyped behavior (e.g. behavior of continuous sniffing, licking, etc.) is developed in an animal by administering Apomorphine. Apomorphine has an agonist action to a dopamine receptor and has frequently been used so as to develop a remedy for schizophrenia, heretofore [C. J. E. Niemegeeres et al., Arch. int. Pharmacodyn. 227, 238–253 (1977) and A. J. Puech et al., Neuropharmacol. 20, 1279–1284 (1981)].

The test was conducted as follows.

Animal used: Wistar strain male rat (body weight: 250–270 g)

Drug used: $^{14}C$-phenylalanine (L-phenyl[1-$^{14}C$]alanine, manufactured by Amrersham Life Science Co.) apomorphine hydrochloride (manufactured by Sigma Chemical Co., Ltd.)

Test method:

The total examples of the test group were six, i.e. the apomorphine administration group of three examples and control group of three examples. $^{14}C$-Phenylalanine (1.5 ml) having a concentration of 1.85 MBq/ml was diluted with distilled water (6 ml) in a fivefold dilution to prepare a solution having a concentration of 0.37 MBq/ml. The resulting solution was orally administered to individuals with a volume of 1 ml per individual rat.

Apomorphine (10 mg) was dissolved in saline to prepare a solution having a concentration of 2 mg/ml. The resulting solution was subcutaneously administered with a volume of 1 ml per individual rat of the apomorphine administration group. On the other hand, only saline was subcutaneously administered to the control group with the same volume as that described above.

An amount of $^{14}CO_2$ derived from the metabolized $^{14}C$-phenylalanine in the breath was determined by trapping the breath in a breath trapping solvent (a mixture wherein 2-aminoethanol and methanol are mixed at 1:3) installed in a metabolism testing device, collecting 1 ml of this solvent in a scintillation vial every fixed time, diluting the solvent with a scintillation cocktail solution (10 ml) and counting a radioactivity with a liquid scintillation counter for β ray.

In the test, each rat was firstly put in a metabolism testing device and, 15 minutes after standing, a breath trapping solvent was collected and a radioactivity was measured. The resulting radioactivity was taken as a value immediately before administration. Immediately after collecting the breath trapping solvent for measuring this value-before-administration, apomorphine and $^{14}C$-phenylalanine were simultaneously administered to rats of the apomorphine administration group. Then, the breath trapping solvent was collected four times every 15 minutes until 60 minutes have passed since administration, and the radioactivity was measured. A value obtained by subtracting the previous value from the resulting radioactivity count (dpm) was statistically treated as a data every predetermined time. Saline of the same volume as that of the above apomorphine solution and $^{14}C$-phenylalanine were simultaneously administered to rats of the control group.

In the statistical treatment, an average and a standard error of data obtained every each group and each collecting time were determined and subjected to a dispersion analysis on the basis of the repeated measurement, and then a difference between groups was statistically assumed.

The test results are shown in FIG. 1. As is apparent from FIG. 1, in the apomorphine administration group, $^{14}CO_2$ in the breath was low in all measured points after administration of $^{14}C$-phenylalanine in comparison with the control group wherein no apomorphine was administered. At 30 minutes after administration, the difference was statistically significant. That is, it has been confirmed by Dunnett's two-tailed test that there is a significant difference between the apomorphine group and control group in a probability of 5%.

Therefore, it has been found that the measurement of the amount of $^{14}CO_2$ in the breath makes it possible to assume the fact that a metabolic rate of phenylalanine is decreased.

Test Example 2
(Test due to animal model of depression)

It was examined whether a metabolism of $^{14}C$-phenylalanine administered orally changes or not by comparing an animal model of depression with a normal animal, using an amount of $^4CO_2$ excreted in a breath as an index.

It is assumed that depression is caused by depression of monoamine nerve transmission in the brain. Since reserpine has a strong monoamine depletion action, symptoms similar to those of depression (e.g. inhibition of spontaneous behavior, reduction in body temperature, lethargy, etc.) is developed when this drug is administered to the animal. Therefore, it has hitherto been used as the animal model of depression [Howard, J. L. et al., : Antidepressants: Neurochemical, behavioral, and clinical perspectives (ed. by Enna, S. J., Malick, J. B. and Richelson, E.), 107–120, Raven Press, New York, 1981].

The test was conducted as follows.
Animal used: Wistar strain male rat (body weight: 250–270 g)
Drug used: $^{14}C$-phenylalanine (L-phenyl[1-$^{14}C$]alanine, manufactured by Amersham Life Science Co.)
Reserpine (Apoplon Inj., 1 mg/ml, manufactured by Daiichi Seiyaku Co., Ltd.)
Test method:

The total examples of the test group were six, i.e. the reserpine administration group of three examples and control group of three examples. $^{14}C$-phenylalanine (1.5 ml) having a concentration of 1.85 MBq/ml was diluted with distilled water (6 ml) in a fivefold dilution to prepare a solution having a concentration of 0.37 MBq/ml. The resulting solution was orally administered to individuals with a volume of 1 ml per individual rat.

Reserpine was subcutaneously administered with a volume of 1 ml/kg per individual rat of the reserpine administration group. Since 16 to 18 hours are required for reserpine to develop the effect, after 18 hours from administration of reserpine, $^{14}C$-phenylalanine was administrated to rats.

On the other hand, only saline was subcutaneously administered to rats of the control group with the same volume as that of reserpine at the same time as that of administration of reserpine.

An amount of $^{14}CO_2$ derived from the metabolized $^{14}C$-phenylalanine in the breath was determined by counting a radioactivity according to the same manner as that described in Test Example 1.

In the test, each rat was firstly put in a metabolism testing device and, at 15 minutes after standing, a breath trapping solvent was collected and a radioactivity was measured. The resulting radioactivity was taken as a value immediately before administration. Immediately after collecting the breath trapping solvent for measuring this value-before-administration, $^{14}C$-phenylalanine was administered to rats. Then, the breath trapping solvent was collected four times every 15 minutes until 60 minutes have passed since administration, and the radioactivity was measured. A value obtained by subtracting the previous value from the resulting radioactivity count (dpm) was statistically treated as a data every time.

In the statistical treatment, an average and a standard error of data obtained every each group and each collecting time were determined and subjected to a dispersion analysis on the basis of the repeated measurement, and then a difference between groups was statistically assumed.

Figure 2:
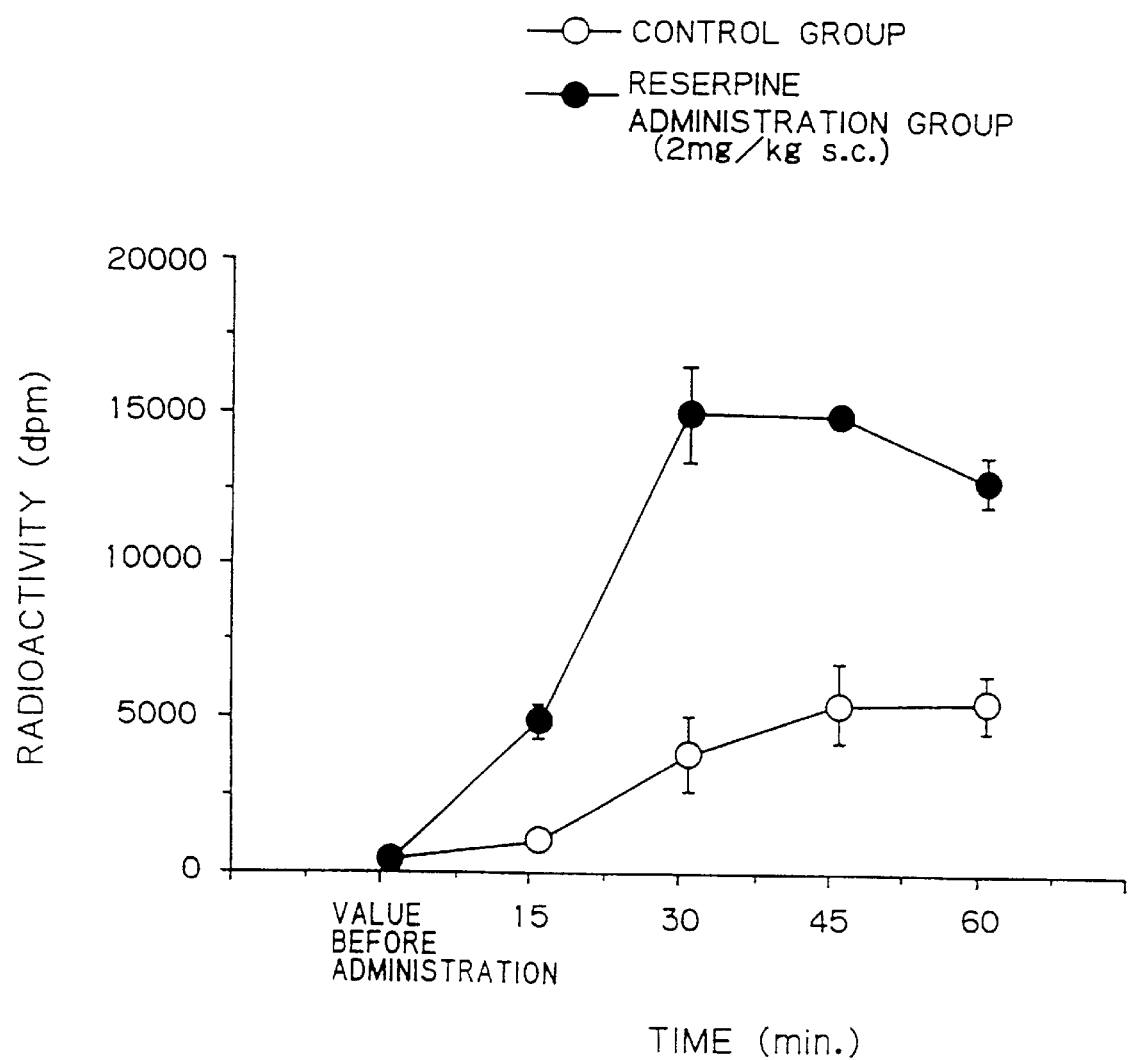
FIG. 2 is a graph illustrating a change in radioactivity of $^{14}CO_2$ in a breath with time after administering $^{14}C$-phenylalanine in the animal model of depression.

The test results are shown in FIG. 2. As is apparent from FIG. 2, in the reserpine administration group, an amount of $^{14}CO_2$ in the breath was high in all measured points after administration of $^{14}C$-phenylalanine in comparison with the control group wherein no reserpine was administered, and the difference was statistically significant. That is, it has been confirmed by Dunnett's two-tailed test that there is a significant difference between the reserpine group and control group in a probability of 0.1%.

Test Example 3
(Test due to animal model of dementia)

It was examined whether a metabolism of $^{14}C$-phenylalanine administered orally changes or not by comparing an animal model of dementia with a normal animal, using an amount of $^{14}CO_2$ excreted in a breath as an index.

It is considered that memory disorder and intellectual function disorder, which are identified as a main symptom of dementia, are caused by depression of neuronal activity of acetylcholine or degeneration/deciduation of nerve cells.

Scopolamine is an antagonist of muscarinic acetylcholine M1 receptor, and has an action of blocking an acetylcholinenerve transmission when incorporated into a central nervous system by peripheral administration. This action can easily cause memory/learning disorder in the animal. Therefore, scopolamine has widely been used for a study on dementia as a drug of developing main mobility of dementia, heretofore [Matsuoka N, et al, J. Pharmacol. Exp. Ther. 263 (2), 436–444 (1992), and Davis, L., et al, J. Med. Chem. 39 (2), 582–587 (1996)].

The test was conducted as follows.
Animal used: Wistar strain male rat (body weight: 250–270 g)
Drug used: $^{14}C$-phenylalanine (L-phenyl[1-$^{14}C$]alanine, manufactured by American Radiolabeled Chemicals Inc.)
Scopolamine hydrobromide (manufactured by Sigma Chemical Co., Ltd.)
Test method:

The total examples of the test group were six, i.e. the scopolamine administration group of three examples and control group of three examples. $^{14}C$-phenylalanine (0.75 ml) having a concentration of 3.7 MBq/ml was diluted with distilled water (6.75 ml) in tenfold dilution to prepare a solution having a concentration of 0.37 MBq/ml. The resulting solution was orally administered to individuals with a volume of 1 ml per individual rat.

Scopolamine (1 mg) was dissolved in saline (1 ml) and the resulting solution was injected to the rat intraperitonealy with a volume of 1 ml/kg. In the control group, only saline was injected to the rat intraperitonealy with the same volume as that of scopolamine.

An amount of $^{14}CO_2$ derived from the metabolized $^{14}C$-phenylalanine in the breath was determined by counting a radioactivity according to the same manner as that described in Test Example 1.

In the test, each rat was firstly put in a metabolism testing device and, 15 minutes after standing, a breath trapping solvent was collected and a radioactivity was measured. The resulting radioactivity was taken as a value immediately before administration. Immediately after collecting the breath trapping solvent for measuring this value-before-administration, $^{14}C$-phenylalanine was administered to rats. Then, the breath trapping solvent was collected four times every 15 minutes until 60 minutes have passed since administration, and the radioactivity was measured. A value obtained by subtracting the previous value from the resulting radioactivity count (dpm) was statistically treated as a data every time.

In the statistical treatment, an average and a standard error of data obtained every each group and each collecting time were determined and subjected to a dispersion analysis on the basis of the repeated measurement, and then a difference in group was statistically assumed.

Figure 3:
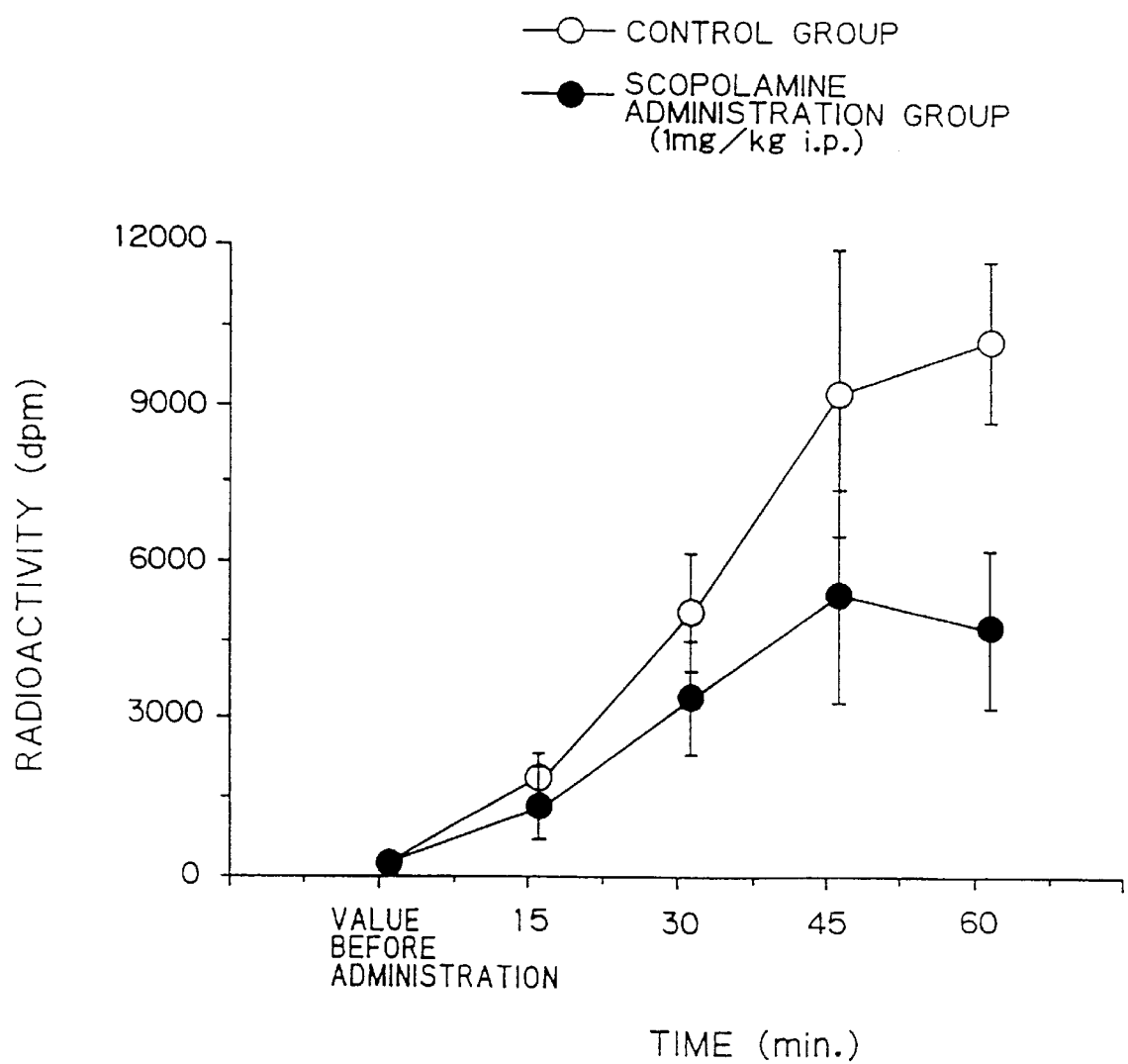
FIG. 3 is a graph illustrating a change in radioactivity of $^{14}CO_2$ in a breath with time after administering $^{14}C$-phenylalanine in the animal model of dementia.

The test results are shown in FIG. 3. As is apparent from FIG. 3, in the scopolamine administration group, an amount of $^{14}CO_2$ in the breath was low at all measured points after administration of $^{14}C$-phenylalanine in comparison with the control group wherein no scopolamine was administered, and the difference was statistically significant.

Example 1

Phenylalanine labeled with ARC at the 1-position (manufactured by Goseihin Co. Ltd.) was administered to a patient suffering from depression and a normal person with a dose of 100 mg/body. At 0, 30, 60, 90, 120, 150 and 180 minutes after administration, a breath (250 ml) was collected in an aluminum bag and a concentration ratio of $^{12}CO_2$ to $^{13}CO_2$ was measured by using a mass spectrometer (manufactured by Finigun Mat Instrument Inc; Breathmat Co.), thereby diagnosing with the measured concentration ratio.

As a result, it has become apparent that depression can be precisely diagnosed according to the diagnosis process using the diagnostic of the present invention.

The reason is that, regarding the patient suffering from depression, an activity of a metabolic enzyme of phenylalanine is lowered at the liver and therefore a metabolism to tyrosine is delayed.

Examples 2 and 3

According to the same manner as that described in Example 1, phenylalanine labeled with $^{13}C$ at the 1-position (manufactured by Goseihin Co. Ltd.) was administered to patients suffering from Alzheimer's disease and schizophrenia in place of the patient suffering from depression, and a normal person with a dose of 100 mg/body. At 0, 30, 60, 90, 120, 150 and 180 minutes after administration, a breath (250 ml) was collected in an aluminum bag and a concentration ratio of $^{12}CO_2$ to $^{13}CO_2$ was measured by using a mass spectrometer (manufactured by Finigun Mat Instrument Inc; Breathmat Co.), thereby diagnosing with the measured concentration ratio.

As a result, it has become apparent that Alzheimer's disease and schizophrenia can be precisely diagnosed according to the diagnosis process using the diagnostic of the present invention.

We claim:

1. A diagnostic for a central nervous system abnormality, comprising a labeled transmitter substance of the central nervous system or a labeled precursor of said transmitter substance, having at least one carbon atom substituted by a carbon isotope, and upon being administered to a living animal by oral administration or injection, functions to diagnose the central nervous system abnormality due to a change in an amount of the carbon isotope contained in the breath of the living animal, wherein said labeled transmitter substance of the central nervous system or its labeled precursor is at least 5-hydroxyindoleacetic acid, a histamine substance, a choline substance or a catecholamine substance, wherein said catecholamine substance is a tyrosine, a dopa, a dopamine, a norepinephrine or an epinephrine.

2. The diagnostic according to claim 1, wherein the histamine substance is a histidine.

3. The diagnostic according to claim 1, wherein the choline substance is a choline, a phosphatidylcholine or an acetylcholine.

4. The diagnostic according to claim 1, wherein the carbon isotope used for labeling is radioactive or non-radioactive.

5. The diagnostic according to claim 1, wherein the central nervous system abnormality is depression, dementia or schizophrenia.

6. A composition to be used as a diagnostic for a central nervous system abnormality, comprising a diagnostically effective amount of a labeled transmitter substance of the central nervous system or a labeled precursor of said transmitter substance, having at least one carbon atom substituted by a carbon isotope, and a pharmaceutically available carrier, wherein said labeled transmitter substance of the central nervous system or its labeled precursor is at least 5-hydroxyindoleacetic acid, a histamine substance, a choline substance or a catecholamine substance, wherein said catecholamine substance is a tyrosine, a dopa, a dopamine, a norepinephrine or an epinephrine.

7. A method for diagnosing a central nervous system abnormality, which comprise administering a diagnostic for a central nervous system abnormality to a living animal by oral administration or injection, and examining a change in an amount of a carbon isotope in the breath of the living animal, by comparing said amount of carbon isotope in the breath of said living animal to the amount of carbon isotope in the breath of the same species of living animal that does not have a central nervous system abnormality, wherein the diagnostic comprises a labeled transmitter substance of the central nervous system or a labeled precursor of said transmitter substance, having at least one carbon atom substituted by the carbon isotope.

8. A method according to claim 7, wherein the amount of the carbon isotope is represented by the ratio of an amount of carbon dioxide which is labeled with a carbon isotope in the breath of the living animal, to that of carbon dioxide which is not labeled with the carbon isotope.

9. A method according to claim 7, wherein the amount of the carbon isotope is represented by the radioactivity of the breath of the living animal.

10. A method according to claim 7, wherein the transmitter substance of the central nervous system or its precursor is a catecholamine substance, a serotonin substance, a histamine substance or a choline substance.

11. A method according to claim 7, wherein the transmitter substance of the central nervous system or its precursor is of 5-hyxdroxyindoleacetic acid, a histamine substance, a choline substance or catecholeamine substance wherein said catecholeamine substance is a tyrosine, a dopa, a dopamine, a norepinephrine or an epinephrine.

12. A method according to claim 7, wherein the central nervous system abnormality is dementia.

13. A method according to claim 7, wherein the central nervous system abnormality is depression.

14. A method according to claim 7 wherein the central nervous system abnormality is Alzheimer's disease.

15. A method according to claim 7, wherein the central nervous system abnormality is schizophrenia.

* * * * *